United States Patent [19]
Stewart et al.

[11] Patent Number: 6,087,353
[45] Date of Patent: Jul. 11, 2000

[54] PHYTOSTEROL COMPOSITIONS AND USE THEREOF IN FOODS, BEVERAGES, PHARMACEUTICALS, NUTRACEUTICALS AND THE LIKE

[75] Inventors: David John Stewart, N. Vancouver; Radka Milanova; Jerzy Zawistowski, both of Vancouver; Simon Howard Wallis, Burnaby, all of Canada

[73] Assignee: Forbes Medi-Tech Inc., Vancouver, Canada

[21] Appl. No.: 09/079,825

[22] Filed: May 15, 1998

[51] Int. Cl.$^7$ .................................................. A61K 31/56
[52] U.S. Cl. .................................... 514/182; 514/824
[58] Field of Search .................................... 514/182, 824

[56] References Cited

PUBLICATIONS

CA 87:157010, Ohsawa, Jul. 1977.

*Primary Examiner*—Kimberly Jordan
*Attorney, Agent, or Firm*—Susan M. N. Ben-Oliel

[57] ABSTRACT

The present invention provides a esterified and subsequently hydrogenated phytosterol composition for use alone or for incorporation into foods, beverages, pharmaceuticals, nutraceuticals, and the like. The composition has the advantage of enhanced solubility/dispersability, increased molar potency and enhanced stability over naturally isolated phytosterol compositions. Methods for the esterification and subsequent hydrogenation of the phytosterols are also provided.

13 Claims, No Drawings

PHYTOSTEROL COMPOSITIONS AND USE THEREOF IN FOODS, BEVERAGES, PHARMACEUTICALS, NUTRACEUTICALS AND THE LIKE

FIELD OF THE INVENTION

This present invention relates to the field of phytosterol-based compositions suitable for incorporation into foods, pharmaceuticals, nutraceuticals and the like and to methods of making the same.

BACKGROUND OF THE INVENTION

While recent advances in science and technology are helping to improve quality and add years to human life, the prevention of atherosclerosis, the underlying cause of cardiovascular disease ("CVD") has not been sufficiently addressed. Research to date suggest that cholesterol may play a role in atherosclerosis by forming atherosclerotic plaques in blood vessels, ultimately cutting off blood supply to the heart muscle or alternatively to the brain or limbs, depending on the location of the plaque in the arterial tree (1,2). Overviews have indicated that a 1% reduction in a person's total serum cholesterol yields a 2% reduction in risk of a coronary artery event (3). Statistically, a 10% decrease in average serum cholesterol (e.g. from 6.0 mmol/L to 5.3 mmol/L) may result in the prevention of 100,000 deaths in the United States annually (4).

Sterols are naturally occurring triterpenoids that perform many critical cellular functions. Phytosterols such as campesterol, stigmasterol and beta-sitosterol in plants, ergosterol in fungi and cholesterol in animals are each primary components of cellular and sub-cellular membranes in their respective cell types. The dietary source of phytosterols in humans comes from plant materials i.e. vegetables and plant oils. The estimated daily phytosterol content in the conventional western-type diet is approximately 60–80 milligrams in contrast to a vegetarian diet winch would provide about 500 milligrams per day.

Phytosterols have received a great deal of attention due to their ability to decrease serum cholesterol levels when fed to a number of mammalian species, including humans. While the precise mechanism of action remains largely unknown, the relationship between cholesterol and phytosterols is apparently due in part to the similarities between the respective chemical structures (the differences occurring in the side chains of the molecules). It is assumed that phytosterols displace cholesterol from the micellar phase and thereby reduce its absorption.

Over forty years ago, Eli Lilly marketed a sterol preparation from tall oil and later from soybean oil called Cytellin™ which was found to lower serum cholesterol by about 9% according to one report (5). Various subsequent researchers have explored the effects of sitosterol preparations on plasma lipid and lipoprotein concentrations (6) and the effects of sitosterol and campesterol from soybean and tall oil sources on serum cholesterols (7). A composition of phytosterols which has been found to be highly effective in lowering serum cholesterol is disclosed in PCT/CA95/00555 and comprises no more than 70% by weight beta-sitosterol, at least 10% by weight campesterol and stigmastanol. It is hypothesized in this patent application (which has already issued to patent in some countries) that there may be some form of synergy between the constituent phytosterols.

Given that phytosterols in various combinations have been proven to have wide clinical and dietary applications in lowering total and low density lipoprotein cholesterol, the key problem now facing researchers in this field is the adaptation of the phytosterol delivery system. Studies have investigated how the form (for example, crystalline, suspension, granular) in which the phytosterols are dosed impacts on their ability to lower serum cholesterol levels. Phytosterols are highly hydrophobic, do not dissolve to any significant degree in the micellar phase in the digestive tract and therefore are not capable of efficiently blocking cholesterol absorption. Oils and fats are capable to a limited but not satisfactory degree of dissolving free phytosterols. Since only solubilized phytosterols inhibit the absorption of cholesterol, this "delivery" problem must be adequately addressed.

Early research focused on grinding or milling the phytosterols in order to enhance their solubility (U.S. Pat. Nos.: 3,881,005 and 4,195,084 both to Eli Lilly). In addition, researchers have looked to the esterification of phytosterols in order to enhance their solubility in delivery systems. German Patent 2035069/Jan. 28, 1971 (analogous to U.S. Pat. No. 3,751,569) describes the addition of phytosterol fatty acid esters to cooking oil. The esterification is carried out between a free sterol and a fatty acid anhydride, with perchloric acid as the catalyst. The significant drawback to this process, along with others, is the use of non-food grade catalysts and reagents.

U.S. Pat. No. 4,588,717 to David E. Mitchell Medical Research Institute describes a vitamin supplement which comprises a fatty acid ester of a phytosterol, wherein the fatty acid forming the ester has from about 18 to 20 carbon atoms in the main carbon chain.

U.S. Pat. No. 5,270,041 to Marigen S. A. teaches the use of small amounts of sterols, their fatty acid esters and glucosides for the treatment of tumours. The method of preparation of these compositions involving the use of hazardous chemical reagents effectively precludes their use in foods or as dietary additives.

Other research has demonstrated that phytostanols, the 5 alpha saturated derivatives of phytosterols, are more effective as therapeutic agents in lowering serum cholesterol on a molecular weight basis than phytosterols (8). Similarly, in a further comparison, sitosterols infused into the GI tract resulted in a 50% reduction in serum cholesterol as opposed to an 85% reduction when sitostanols were infused (9). The advantages of stanols over sterols with respect to inhibition of cholesterol absorption from the GI tract are two-fold. Firstly, stanols are more chemically stable than their unsaturated counterparts in heat and air due to the absence of carbon-carbon bonds in the former. Secondly, stanols are more effective at lowering serum cholesterol on a molecular weight basis than their unsaturated counterparts.

U.S. Pat. No. 5,502,045 to Raision Tehtaat Oy AB (hereinafter the "Raision Patent") describes the preparation of a beta-sitostanol fatty acid ester mixture prepared by interesterifying beta-sitostanol with a fatty acid ester containing from 2 to 22 carbon atoms in the presence of an interesterification catalyst. This process renders the sitostanol appreciably more soluble in fats and oils.

South African Patent Application 967616 also to Raision Tehtaat Oy AB (hereinafter the "SA Raision Patent") describes a similar composition to that in the Raision Patent but which further contains at least 10% campestanol obtained by hydrogenation of the phytosterol mixture.

U.S. Pat. No. 5,244,887 to Straub discloses a method of making a food additive composition which comprises dissolving a stanol (sitostanol; clionastanol; 22,23-dihydrobrassicastanol; campestanol and mixtures thereof)

with an edible solubilizing agent, an anti-oxidant and a carrier or dispersant.

Although the Raision Patent and the Raision SA Patent both attempt to produce a phytostanol delivery system which is stable and effective, there are significant problems with the long-term stability of these esterified products due to the ultimate oxidation of the unsaturated fatty acid moiety.

It is an object of the present invention to obviate or mitigate the above disadvantages.

SUMMARY OF THE INVENTION

The present invention provides a composition suitable for use alone or for incorporation into foods, beverages, pharmaceuticals, nutraceuticals and the like which comprises one or more esterified and subsequently hydrogenated phytosterols.

The present invention further comprises foods, beverages, pharmaceuticals, nutraceuticals and the like which comprise one or more esterified and subsequently hydrogenated phytosterols. These "formulations" include, but are not limited to, the composition incorporated into edible oils and fat-based foods (such as margarines, butter, mayonnaise, dressing, shortenings, and cheeses), and formed into suspensions, emulsions, microemulsions, liposomes, niosomes and general hydrated lipid phases. The composition additionally may be incorporated into numerous pharmaceutical dosage forms as described in detail below.

The present invention further comprises the use of a composition which comprises one or more esterified and subsequently hydrogenated phytosterols to lower serum cholesterol in animals, including humans.

The present invention further comprises methods of making a composition suitable for incorporation into foods, beverages, pharmaceuticals, nutraceuticals and the like which comprises condensing a suitable aliphatic acid with a phytosterol to form a phytosterol ester and subsequently hydrogenating the phytosterol ester to form a hydrogenated phytosterol ester.

The composition of the present inventions which comprises one or more esterified and subsequently hydrogenated phytosterols has marked advantages over the phytosterol compositions previously known and described, particularly those compositions taught in the Raision Patent and the SA Raision Patent. The composition of the present invention not only enhances the solubility and dispersability of phytosterols in lipid or fat-based systems and aqueous systems and increases the molar potency of phytosterols as agents to lower serum cholesterol but also greatly improves and extends the stability and shelf-life of the composition, alone and in association with other forms of conveyance or administration. These advantages and their commercial implications are described in more detail below.

PREFERRED EMBODIMENTS OF THE INVENTION

According to one aspect of the present invention, there is provided a composition suitable for use alone or for incorporation into foods, beverages, pharmaceuticals, nutraceuticals and the like which comprises one or more esterified and subsequently hydrogenated phytosterols.

The key feature of this invention, which affords the advantages of enhanced solubility/dispersability, increased molar potency and particularly enhanced stability, hinges on the esterification of the phytosterols prior to hydrogenation (i.e. saturation). In this way, all unsaturated bonds not only in the phytosterol ring of the ester but in the aliphatic acid moiety are hydrogenated and thereby significantly protected from the effects of oxidation. The resultant composition is also protected from microbial oxidation and/or degradation which is critical when the composition is incorporated into foods such as cheeses and yogurt. In addition, the composition of the present invention is more heat stable and therefore amenable to many food, beverage, pharmaceutical, and nutraceutical processing techniques. The saturation of both the aliphatic acid moiety and phytosterol ring also enhances the solubility of the composition, even without further treatments. Furthermore, this enhanced degree of saturation overcomes the tendency in phytosterols to develop bitterness in aqueous systems which is of importance in the field of preparing comestibles. None of the prior researchers have explored or appreciated the advantages of an esterified and subsequently hydrogenated phytosterol composition.

As used herein, the term "phytosterol" includes all phytosterols without limitation, for example: sitosterol, campesterol, stigmasterol, brassicasterol, desmosterol, chalinosterol, poriferasterol, clionasterol and all natural or synthesized forms and derivatives thereof, including isomers. It is to be understood that modifications to the phytosterols i.e. to include side chains also falls within the purview of this invention. It is also to be understood that this invention is not limited to any particular combination of phytosterols forming a composition. In other words, any phytosterol alone or in combination with other phytosterols in varying ratios as required depending on the nature of the ultimate formulation may be subject to the esterification and subsequent hydrogenation method of the present invention. For example, the composition described in PCT/CA95/00555 which comprises no more than 70% by weight beta-sitosterol, at least 10% by weight campesterol and stigmastanol may be esterified and hydrogenated to yield a stable and favourably soluble product for incorporation into foods.

The phytosterols for use in this invention may be procured from a variety of natural sources. For example, they may be obtained from the processing of plant oils (including aquatic plants) such as corn oil and other vegetable oils), wheat germ oil, soy extract, rice extract, rice bran, rapeseed oil, sesame oil and fish oil. Without limiting the generality of the foregoing, it is to be understood that there are other sources of phytosterols such as marine animals from which the composition of the present invention may be prepared. U.S. patent Ser. No. 4,420,427 teaches the preparation of sterols from vegetable oil sludge using solvents such as methanol. Alternatively, phytosterols may be obtained from tall oil pitch or soap, by-products of the forestry practise as described in PCT/CA95/00555, incorporated herein by reference.

The order of the steps in the method of the present invention is of critical importance. Esterification of the phytosterol must occur before the hydrogenation step. This way, the entire ester is saturated during hydrogenation and not just the phytosterol component, thereby removing all unstable double or pi bonds from the molecule.

To form the phytosterol esters, one or more suitable aliphatic acids or their esters with low boiling alcohols are condensed with the phytosterols. A wide variety of aliphatic acids or their esters may be used successfully within the scope of the present invention and include all aliphatic acids consisting of one or more alkyl chains with one or more terminal carboxyl groups. These aliphatic acids may be natural or synthetic and are represented by the following chemical formulae:

a) R1—COOH (monocarboxylic acid) wherein:
   R1 is an unbranched saturated alky group, represented by CH3—, CH3CH2— or CH3(CH2)nCH2— WHERE n=3–25; or
   R1 is a branched saturated alkyl group represented by CnH2n+1— where n=1–25 is the number of carbon atoms contained in the group R1; the branching typically refers, but is not limited to one or more methyl group side chains (branches); or
   R1 is an unbranched or branched unsaturated alkyl group, represented by the formula CnH2n—2m+1, where n=1–25 is the number of carbon atoms in R1 and m=degree of unsaturation; or
b) HOOC—R2—COOH is a dicarboxylic acid wherein:
   R2 is an unbranched saturated alkly group, represented by —CH2—, or —CH2CH2—, or —CH2(CH2)nCH2 where n=3–25; or
   R2 is a branched saturated alkyl group represented by —CnH2n— where n=1–25 is the number of carbon atoms contained in the group R2; the branching typically refers, but is not limited to, one or more methyl group side chains (branches); or
   CnH2n—2m, where n=1–25 is the number of carbon atoms in R2 and m=degree of unsaturation; or
c) a tricarboxylic acid represented by the formula:

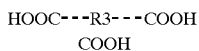

wherein, in this formula:
   R3 is a branched saturated alkyl group represented by —CnH2n—1— where n=1–25 is the number of carbon atoms contained in the group R3; the branching typically refers, but is not limited to, one or more methyl group side chains (branches); or
   R3 is a branched unsaturated alkyl group, represented by CnH2n—2m—1— wherein n=1–25 is the number of carbon atoms in R3 and m=the degree of unsaturation; or
d) a mono-, di-, or tricarboxylic acid as defined above, which may contain one, two or three hydroxyl groups in the molecule.

In a preferred form, the aliphatic acid is either a straight-chain or branched unsaturated or saturated fatty acid selected, inter alia, from the following list: valeric acid, isovaleric acid, sorbic acid, isocaproic acid, lauric acid, myrestic acid, palmitic acid, stearic acid, caproic acid, ascorbic acid, arachidic acid, behenic acid, hexacosanoic acid, octacosanoic acid, pentadecanoic acid, erucic acid, linoleic acid, linolenic acid, arachidonic acid, acetic acid, citric acid, tartaric acid, palmitoleic acid and oleic acid. The most preferable fatty acids within the scope of the present invention are linoleic acid, linolenic acid and arachidonic acid which may be obtained from natural sources such as safflower oil, sunflower oil, olive oil and corn oil (linoleic acid), safflower oil, sunflower oil, olive oil and jojoba oil (linolenic acid and arachidonic acid) and rapeseed oil (erucic acid).

A particular advantage in using fatty acids to form esterifed and subsequently hydrogenated phytosterols, i.e. saturated fats, in accordance with the present invention lies in the fact that saturated fats increase lipoprotein lipase activity. The activity of this latter enzyme reduces visceral fat formation.

To form a phytosterol ester in accordance with the present invention, the selected phytosterol and aliphatic acid or its ester with volatile alcohol are mixed together under reaction conditions to permit condensation of the phytosterol with the aliphatic acid to produce an ester. A most preferred method of preparing these esters which is widely used in the edible fat and oil industry is described in U.S. Pat. No. 5,502,045 (which is incorporated herein by reference). As no substances other than the free phytosterol, a fatty acid ester or mixture thereof and an interesterification catalyst like sodium ethylate are used, the technique is highly suitable for preparing products ultimately for human consumption. In overview, this preferred method, adapted for use within the present invention, comprises heating the phytosterol(s) with a vegetable oil fatty acid ester (preferably a methyl ester) at a temperature from 90–120° C. and subsequently adding a suitable catalyst such as sodium ethylate. The catalyst is then removed/destroyed by any one of the techniques known in the art e.g. adding water and/or filtration/centrifugation.

Another method which may be used in accordance with the present invention is described in U.S. Pat. No. 4,588,717, which is also incorporated herein by reference. A preferred method is to mix the phytosterol and the fatty acid together bringing the mixture to a temperature of from about 15° C. to about 45° C. at about atmospheric pressure for approximately one to three hours.

Once the phytosterol ester is formed in accordance with the present invention it must then be hydrogenated. The conversion of the phytosterol ester to its saturated form may be achieved by one of many known hydrogenation techniques (10, incorporated herein by reference) based on the use of Pd/C catalyst in organic solvents. Other suitable catalysts include platinum and Raney nickel. When this step is carried out under optimal conditions, only very small amounts of unsaturated sterol esters remain unconverted.

Within the scope of the present invention, it is possible to produce two classes of esterified and subsequently hydrogenated phytosterol compositions. The first class of composition, hereinafter referred to as the oil-based composition derives from a method in which the esterification step proceeds in oil, for example, a vegetable oil. This is the esterification process generally described in U.S. Pat. No. 5,502,045. The second class of composition, hereinafter referred to as the solvent-derived composition is generated by a method in which the esterification step proceeds in a suitable solvent, including an aqueous solution and not oil. The end product of these two classes, although both esterified and subsequently hydrogenated phytosterols, are each suitable for use in various delivery systems as disclosed further below.

Oil-Based Composition

The preferred method of preparing the oil-based composition comprises selecting one or more phytosterols and esterifying these phytosterols in a suitable oil. Commonly known interesterification techniques are provided in references 11, 12 and 13. The resultant esterified phytosterol composition is then hydrogenated. Although the oil-based composition of the present invention may be used alone or in various delivery systems, greatest efficacy is achieved when the esterified and subsequently hydrogenated phytosterols are further treated so as to ensure even distribution throughout the food, beverage, pharmaceutical or nutraceutical to which they are added. This is most readily accomplished by first enhancing the solubility and/or dispersability of the composition in a delivery system. Such enhancement may be achieved by a number of suitable means such as, for example, solubilizing or dispersing the composition to form emulsions, solutions and dispersions and self-emulsifying systems and the like as described further below.

Emulsions

Emulsions are finely divided or colloidal dispersions comprising two immiscible phases, e.g. oil and water, one of which (the internal or discontinuous phase) is dispersed as droplets within the other (external or discontinuous phase). Thus an oil-in-water emulsion consists of oil as the internal phase, dispersed water as the external phase, the water-in-oil emulsion being the opposite.

A wide variety of emulsified systems may be formed which comprise the composition of the present invention including standard emulsions, microemulsions and those which are self-emulsifying (emulsify on exposure to agitated aqueous fluids such as gastric or intestinal fluids).

Generally, emulsions may include oil and water phases, emulsifiers, emulsion stabilizers and optionally preservatives, flavouring agents, pH adjusters and buffers, chelating agents, antifoam agents, tonicity adjusters and anti-oxidants. Suitable emulsifiers (wherein bracketed numerals refer to the preferred HLB values) include: anionic surfactants such as alcohol ether sulfates, alkyl sulfates (30–40), soaps (12–20) and sulfosuccinates; cationic surfactants such as quaternary ammonium compounds; zwtterionic surfactants such as alkyl betaine derivatives; amphoteric surfactants such as fatty amine sulfates, difatty alkyl triethanolamine derivatives (16–17); and nonionic surfactants such as the polyglycol ether derivatives of aliphatic or cycloaliphatic alcohols, saturated fatty acids and alkyphenols, water-soluble polyethyleneoxy adducts onto polypropylene glycol and alkyl polypropylene glycol, nonylphenol polyethoxyethanols, castor oil polyglycol ethers, polypropylene/polyethylene oxide adducts, tributylphenoxy-polyethoxyethanol, polyethylene glycol, octylphenoxy-polyethoxethanol, lanolin alcohols, polyoxyethylated (POE) alkyl phenols, POE fatty amides, POE fatty alcohol ethers, POE fatty amines, POE fatty esters, poloxamers (7–19). POE glycol monoethers (13–16), polysorbates and sorbitan esters. This list is not intended to be exhaustive as other emulsifiers are equally suitable.

Appropriate emulsion stabilizers include, but are not limited to, lyophilic colloids such as polysaccharides (e.g. acacia, agar, alginic acid, carrageenin, guar gum, karaya gum, tragacanth xanthan gum), amphoterics (e.g. gelatin) and synthetic or semi-synthetic polymers (e.g. carbomer resins, cellulose ethers, carboxymethyl chitin, polyethylene glycol-n (ethylene oxide polymer H(OCH2CH2)nOH); finely divided solids including clays (e.g. attapulgite, bentonite, hectorite, kaolin, magnesium aluminum silicate and montmorillonite), microcrystalline cellulose oxides and hydroxides (e.g. aluminum hydroxide, magnesium hydroxide and silica); and cybotactic promoters/gellants including amino acids, peptides, proteins lecithin and other phospholipids and poloxamers.

Suitable anti-oxidants for use in the formation of emulsions include: chelating agents such as citric acid, EDTA, phenylalanine, phosphoric acid, tartaric acid and tryptophane; preferentially oxidized compounds such as ascorbic acid, sodium bisulfite and sodium sulfite; water soluble chain terminators such as thiols and lipid soluble chain terminators such as alkly gallates, ascorbyl palmitate, t-butyl hydroquinone, butylated hydroxyanisole, butylated hydroxyrtoluene, hydroquinone, nordihydroguaiaretic acid and alpha-tocopherol. Suitable preservatives, pH adjustment agents, and buffers, chelating agents, osmotic agents, colours and flavouring agents are discussed hereinbelow under "Supensions", but are equally applicable with respect to the formation of emulsions.

The general preparation of emulsions is as follows: the two phases (oil and water) are separately heated to an appropriate temperature (the same in both cases, generally 5–10° C. above the melting point of the highest melting ingredients in the case of a solid or semi-solid oil, or where the oil phase is liquid, a suitable temperature as determined by routine experimentation). Water-soluble components are dissolved in the aqueous (water) phase and oil-soluble components are dissolved in the oil phase. To create an oil-in water emulsion, the oil phase is vigorously mixed into the aqueous phase to create a suitable dispersion and the product is allowed to cool at a controlled rate with stirring. A water-in-oil emulsion is formed in the opposite fashion i.e. the water phase is added to the oil phase. When hydrophillic colloids are a part of the system as emulsion stabilizers, a phase inversion technique may be employed whereby the colloid is mixed into the oil phase rather than the aqueous phase, prior to addition to the aqueous phase. In using the oil-based composition of the present invention, which is semi-solid, it is preferred to add the composition to the oil phase prior to heating.

Microemulsions, characterized by a particle size at least an order of magnitude smaller (10–100 nm) than standard emulsions and defined as "a system of water, oil and amphiphile which is a single optically isotropic and thermodynamically stable liquid" (14), may also be formed comprising the composition of the present invention. In a preferred form, the microemulsion comprises a surfactant or surfactant mixture, a co-surfactant,(usually a short chain alcohol) the oil-based composition of the present invention, water and optionally other additives.

This system has several advantages as a delivery system for the oil-based composition of the present invention. Firstly, microemulsions tend to be created spontaneously, that is, without the degree of vigorous mixing required to form standard emulsions. From a commercial perspective, this simplifies the manufacturing process. Secondly, microemulsions may be sterilized using microfiltration techniques without breaking the microstructure due to the small diameter of the microdroplets. Thirdly, microemulsions are highly thermodynamically stable. Fourthly, microemulsions possess high solubilizing power which is particularly important as they allow for an increased solubilization of the poorly hydrosoluble phytostanol esters.

Surfactant or surfactant mixtures which are suitable for use in the formation of microemulsions can be anionic, cationic, amphoteric or non-ionic and possess HLB (hydrophile-lipophile balance) values within the range of 1–20, more preferably in the ranges 2–6 and 8–17. Especially preferred agents are non-ionic surfactants, selected from the group consisting of polyglycol ether derivatives of aliphatic or cycloaliphatic alcohols, saturated fatty acids and alkyphenols, water-soluble polyethyleneoxy adducts onto polypropylene glycol and alkyl polypropylene glycol, nonylphenol polyethoxyethanols, castor oil polyglycol ethers, polypropylene/polyethylene oxide adducts, tributylphenoxy-polyethoxethanol, polyethylene glycol, octylphenoxy-polyethoxyethanol, lanolin alcohols, polyoxyethylated (POE) alkyl phenols, POE fatty amides, POE fatty alcohol ethers, POE fatty amines, POE fatty esters, poloxamers (7–19), POE glycol monoethers (13–16), polysorbates and sorbitan esters.

There are many methods known and used by those skilled in the art for making microemulsions. In a preferred method of forming microemulsions of the present invention, a surfactant, a co-surfactant and the oil-based composition (pre-dissolved in a suitable proportion of an appropriate oil) is mixed and then titrated with water until a system of desired transparency is obtained.

In a further preferred embodiment, the formation of microemulsions may be achieved by mixing the oil-based compositions with hydrotropic agents and food-grade surfactants (refer to 15).

Solutions and Dispersions

The oil-based composition of the present invention may be dissolved or dispersed in a suitable oil vehicle and used in this form, for example, in general food usage, in basting meats and fish, and for incorporation into animal feeds.

Self-Emulsifying Systems

The oil-based composition may be mixed with appropriate excipients, for example, surfactants, emulsion stabilizers (described above) and the like, heated (if necessary) and cooled to form a semi-solid product capable of forming a spontaneous emulsion on mixing with water. This semi-solid product may be used in numerous other forms such as filler material in two-piece hard or soft gelatin capsules, or may be adapted for use in other delivery systems.

Solvent-Derived Composition

As described above, the solvent-derived composition differs from the oil-based composition in that the esterification and hydrogenation steps occur in a solvent and not an oil. This solvent may be any suitable organic or non-organic solvent without limitation, including water. After hydrogenation of the esterified phytosterol and subsequent isolation and purification, this solvent-derived composition may be used effectively alone or in a physically modified form to lower serum cholesterol. In physically modifying the solvent-derived composition, the ultimate goal is the same as discussed above with respect to the oil-based composition, that is, the enhancement of solubility and dispersability, of the composition so as to ensure even distribution of the esterified phytostanols throughout the food, beverage, pharmaceutical or nutraceutical to which they are added.

Generally, the preparation of the solvent-derived composition comprises selecting one or more phytosterols and esterifying the phytosterols in suitable solvent (aqueous organic or a combination of both) by either of two preferred methods. In a first method, the selected phytosterol(s) derived from, for example, vegetable oil, is added to an appropriate acid anhydride, such as acetic anhydride and then heated, cooled and stirred. In a second method, the phytosterol(s) is dissolved in an appropriate solvent such as acetic acid, acetic anhydride and the like. The esterified product is then hydrogenated by any one of the techniques known and applied in the art. After the hydrogenation step, it is preferred in this embodiment that isolation techniques be employed to obtain a solid powder through precipitation, filtration and drying or by other conventional work-up techniques.

Thereafter, the solvent-derived composition, in powder form, may be incorporated directly into foods, beverages, pharmaceuticals, nutraceuticals and the like or alternatively, may be physically modified as described below to enhance the solubility and dispersability of the composition. It is to be understood that the techniques of solubilizing or dispersing the oil-based composition to form emulsions, solutions and dispersions and self-emulsifying systems may be adapted and applied to the solvent-derived composition. Likewise, the solubilizing techniques described below as being of preferred use with respect to the solvent-derived composition may equally be used with the oil-based composition of this invention. Additional techniques of enhancing the rate and degree of solubility of the solvent-derived composition include, without limitation: reducing particle size by mechanical grinding (milling, micronisation etc..), lyophilizing, spray drying, controlled precipitating, or a combination thereof; forming solid dispersions, suspensions, hydrated lipid systems, inclusion complexations with cyclodextrins, using hydrotopes and formulations with bile acids and their derivatives.

Reducing Particle Size

Many techniques of particle size reduction are suitable for use within the present invention including, inter alia, dry milling, micropulverization, fluid energy grinding, controlled precipitation, lyophilisation and spray-drying. Each of these techniques is well known in the art and will not be discussed in any detail other than to provide reference to 20 and 21, the former showing preferred processes of spray-drying and the latter summarizing the other techniques listed above.

It has been found that reducing the particle size to under 500 um and most preferably under 20 um allows suitable dispersability/solubility of the composition in the carriers and dosage forms described further below.

Solid Dispersions

An alternative means of increasing the solubility/dispersability of the solvent-derived composition involves the use of solid dispersion systems. These dispersions may include molecular solutions (eutectics), physical dispersions or a combination of both.

For example, solid dispersions may typically be prepared by utilizing water-soluble polymers as carriers. Without limitation, these carriers may include, either alone or in combination: solid grade polyethylene glycols (PEG's), with or without the addition of liquid grade PEG's; polyvinylpyrrolidones or their co-polymers with vinyl acetate and cellulose ethers and esters. Other excipients, such as additional members of the glycol family e.g. propylene glycol, polyols, e.g. glycerol etc.. may also be included in the dispersions.

Solid dispersions may be prepared by a number of ways which are familiar to those in the art. These include, without limitation, the following methods:

(a) fusing the ingredients, followed by controlled cooling to allow solidification and subsequent mechanical grinding to produce a suitable powder. Alternatively, the molten (fused) dispersion may be sprayed into a stream of cooled air in a spray drier to form solid particles (prilling) or passed through an extruder and spheroniser to form solid masses of a controlled particle size. In a further alternative, the molten dispersion is filled directly into two-piece hard gelating capsules;

(b) dissolving the ingredients in a suitable solvent system (organic, mixed organic, organic-aqueous) and then removing the solvents e.g. by evaporating at atmospheric pressure or in vacuo, spray drying, lyophilizing and the like; or, in a variation of the foregoing, and (c) dissolving the ingredients in a suitable solvent system, subsequently precipitating them from solution by the use of an immiscible solvent in which the ingredients have little or no solubility, filtration, removing the solvent, drying and optionally grinding to provide a suitable powder form.

Other commercially available agents for enhancing solubility of the phytosterol composition through the formation of solid dispersions are considered to fall within the purview of this application. For example, the commercial excipient marketed under the trade-mark Gelucire™ by Gattefosse comprising saturated polyglycolised glycerides may readily be used herein.

Suspensions

Suspensions, which may be used to enhance the solubility and/or dispersability of the solvent-derived composition, comprise a solid, perhaps finely divided, internal phase dispersed in an oily or aqueous external phase (the vehicle). In addition, the solid internal phase may be added to an emulsion as described above during its formation to produce a delivery system having properties common to both suspensions and emulsions.

Numerous excipients, which are commonly used in the art, may be suitable for producing a suspension within the scope of the present invention. Typically, a suspension comprises an oily or aqueous vehicle, the dispersed (suspended) internal phase, dispersing and/or wetting agents (surfactants), pH adjustment agents/buffers, chelating agents, antioxidants, agents to adjust ionic strength (osmotic agents) colours, flavours, substances to stabilize the suspension and increase viscosity (suspending agents) and preservatives.

Appropriate vehicles include, but are not limited to: water, oils, alcohols, polyols, other edible or food grade compounds in which the phytosterol composition is partially or not soluble and mixtures thereof. Appropriate dispersing agents include, but are not limited to: lecithin; phospholipids; nonionic surfactants such as polysorbate 65, octoxynol-9, nonoxynol-10, polysorbate 60, polysorbate 80, polysorbate 40, poloxamer 235, polysorbate 20 and poloxamer 188; anionic surfactants such as sodium lauryl sulfate and docusate sodium; fatty acids, salts of fatty acids, other fatty acid esters, and mixtures thereof.

Agents/buffers for pH adjustment include citric acid and its salts, tartaric acid and its salts, phosphoric acid and its salts, acetic acid and its salts, hydrochloric acid, sodium hydroxide and sodium bicarbonate. Suitable chelating agents include edetates (disodium, calcium disodium and the like), citric acid and tartaric acid. Suitable antioxidants include ascorbic acid and its salts, ascorbyl palmitate, tocopherols (especially alpha-tocopherol), butylated hydroxytoluene, butylated hydroxyanisole, sodium bisulfite and metabisulfite. Suitable osmotic agents include monovalent, divalent and trivalent electrolytes, monosaccharides and disaccharides. Suitable preservatives include parabens (Me, Et, Pr, Bu), sorbic acid, thimerosal, quaternary ammonium salts, benzyl alcohol, benzoic acid, chorhexidine gluconate and phenylethanol. Colours and flavours may be added as desired and may be selected from all nature, natural-identical and synthetic varieties.

Suitable solubilizing agents include all food grade oils such as plant oils, marine oils (such as fish oil) and vegetable oils, monoglycerides, diglycerides, triglycerides, tocopherols and the like and mixtures thereof.

Hydrated Lipid Systems

In a further embodiment of the present invention, the solubility/dispersability of the solvent-derived composition may be enhanced by the formation of phospholipid systems such as liposomes and other hydrated lipid phases, by physical inclusion. This inclusion refers to the entrapment of molecules without forming a covalent bond and is widely used to improve the solubility and subsequent dissolution of active ingredients.

Hydrated lipid systems, including liposomes, can be prepared using a variety of lipid and lipid mixtures, including phospholipids such as phosphatidylcholine (lecithin), phosphodiglyceride and sphingolipids, glycolipids, cholesterol and the like. The lipids may preferably be used in combination with a charge bearing substances such as charge-bearing phospholipids, fatty acids, and potassium and sodium salts thereof in order to stabilize the resultant lipid systems. A typical process of forming liposomes is as follows:

1) dispersion of lipid or lipids and the solvent-derived composition of the present invention in an organic solvent (such as chloroform, dichloromethane, ether, ethanol or other alcohol, or a combination thereof). A charged species may be added to reduce subsequent aggregation during liposome formation. Antioxidants (such as ascorbyl palmitate, alpha-tocopherol, butylated hydroxytoluene and butylated hydroxyanisole) may also be added to protect any unsaturated lipids, if present;

2) filtration of the mixture to remove minor insoluble components;

3) removal of solvents under conditions (pressure, temperature) to ensure no phase separation of the components occur;

4) hydration of the "dry" lipid mixture by exposure to an aqueous medium containing dissolved solutes, including buffer salts, chelating agents, cryoprotectorants and the like; and 5) reduction of liposome particle size and modification of the state of lamellarity by means of suitable techniques such as homogenization, extrusion etc..

Any procedure for generating and loading hydrated lipid with active ingredients, known to those skilled in the art, may be employed within the scope of this invention. For example, suitable processes for the preparation of liposomes are described in references 18 and 19, both of which are incorporated herein by reference. Variations on these processes are described in U.S. Pat. No. 5,096,629 which is also incorporated herein by reference.

U.S. Pat. No. 4,508,703 (also incorporated herein by reference) describes a method of preparing liposomes by dissolving the amphiphillic lipidic constituent and the hydrophobic constituent to form a solution and thereafter atomizing the solution in a flow of gas to produce a pulverent mixture.

Cyclodextrin Complexes

Cyclodextrins are a class of cyclic oligosaccharide molecules comprising glucopyranose sub-units which may be used to form inclusion complexes with the solvent-derived composition. The molecular shape of cyclodextrin is a torus having a hydrophobic centre and relatively hydrophilic outer surface. In aqueous solutions, both the inner and outer surfaces attract water and the hydrogen bonds within the cavity of the torus attract, thereby distorting the cyclodextrin. This distorted configuration represents a high energy state which will readily accept a "guest" molecule such as the esterified and subsequently hydrogenated phytosterol of this invention via non-covalent bonding. Since the esterified and subsequently hydrogenated phytosterol formed within the process of this invention is quite hydrophobic and insoluble, it will readily form such a complex with cyclodextrin. The complex so formed often confers properties of improved solubility, dispersability, stability (chemical, physical and microbiological), bioavailability and decreased toxicity on the guest molecule (here, the composition of the present invention).

Cyclodextrins are cyclic oligosaccharides composed of dextrose units joined through a 1–4 bond such as alpha, beta and gamma cyclodextrin, carboxymethyl-beta-cyclodextrin, carboxymethyl-ethyl-beta-cyclodextrin, diethyl-beta-cyclodextrin, dimethyl-beta-cyclodextrin, methyl-beta-cyclodextrin, random methyl-beta-cyclodextrin, glucosyl-beta-cyclodextrin, maltosyl-beta-cyclodextrin, hydroxyethyl-beta-cyclodextrin, hydroxypropyl-beta-cyclodextrin and sulfobutylether-beta-cyclodextrin. In other words, the external hydroxyl substituents of the cyclodextrin molecule may be modified to form derivatives having improved solubility in aqueous media and to have other desired advantages such as decreased toxicity etc. Other types of chemical modification known to those skilled in the art are also within the purview of the present invention.

There are a number of ways to produce a cyclodextrin complex, however, three basic ways are described herein. It may be necessary to dissolve the cyclodextrin and the molecules of the present composition in an aqueous or mixed aqueous-organic solution, followed possibly by heating; or by kneading, slurring or mixing the cyclodextrin and guest molecule in a suitable device with the addition of an appropriate quantity of aqueous, organic or mixed aqueous-organic liquid, optionally with heating; or by physically admixing the cyclodextrin and guest molecule using a suitable mixing device. Isolation of the inclusion complex so formed may be achieved by co-precipitation, filtration and drying; extrusion/spheronisation and drying; subdivision of tie moist mass and drying; spray drying; lyophilization or by other suitable techniques depending on the process used to form the cyclodextrin complex. A further optional step of mechanically grinding the isolated solid complex may be employed.

These cyclodextrin/phytosterol composition complexes enhance the solubility and dissolution rate and increase the stability of the composition formed within the scope of the present invention. For a review of cyclodextrin complexation, please refer to 22.

Complexation with Bile Salts

Bile acids, their salts and conjugated derivatives, suitably formulated, may be used to solubilize both the oil-based and solvent-derived compositions of the present invention, thereby improving the solubility and dispersion characteristics of these compositions. Examples of suitable bile acids include: cholic acid, chenodeoxycholic acid, deoxycholic acid, dehydrocholic acid, and lithocholic acid. Examples of suitable bile salts include: sodium cholate, sodium deoxycholate and their other salt forms. Examples of suitable conjugated bile acids include: glycochenodeoxycholic acid, glycholic acid, taurochenodeoxycholic acid, taurocholic acid, taurodeoxycholic acid and their salts.

A suitable system for solubilizing both the oil-based or solvent-derived compositions of the present invention consists of the composition plus one or more bile acids, salts or conjugated bile acids. Further materials may be added to produce formulations having additional solubilization capacity. These materials include, but are not limited to: phospholipids, glycolipids and monoglycerides. These ingredients may be formulated either in the solid phase or by the use of suitable solvents or carrier vehicles, with appropriate isolation and, optionally, particle size reduction using techniques described hereinabove.

Since bile acids and their derivatives have an unpleasant taste and may be irritating to the mucous membranes of the stomach and upper regions of the gastro-intestinal tract, a suitable enteric coating may be applied to the solid formulation particulates, using techniques known to those skilled in the art. Typical enteric coatings include, inter alia: cellulose acetate phthalate, cellulose acetate trimellitiate, hydroxyproplmethylcellulose phthalate, hydroxyproplmethylcellulose acetate succinate, poly (vinylaceate phthalate), acrylate polymers and their derivatives (e.g. appropriate members of the Eudragit series), ethylcellulose or combinations thereof. Additional excipients may be added to the coating formulation to modify membrane functionality or to aid in the coating process (e.g. surfactants, plasticisers, channeling agents, permeability modifiers and the like). Coating formulation vehicles may comprise aqueous or organic systems, or mixtures of both.

Hydrotopic Complexation

Compounds which are capable of opening up the water structure associated with hydrophobic (lipophilic) and other molecules are referred to as hydrotopes. These compounds may be used to enhance the aqueous solubility of poorly water-soluble substances such as phytosterols, phytostanols and their esters. Examples of hydrotopes include, inter alia, sodium benzoate, sodium hydroxybenzoates, sodium salicylate, nicotinamide, sodium nicotinate, sodium gentisate, gentisic acid ethanolamide, sodium toluates, sodium aminobenzoates, sodium anthranilate, sodium butylmonoglycolsulfate, resorcinol and the like.

Complex formation, which is non-covalent in nature, may be achieved by mixing appropriate ratios of the solvent-derived composition and the hydrotope or mixtures thereof in a suitable liquid vehicle, which may be aqueous, organic or a combination of both. Additional excipients such as surfactants, polyol, disaccharides etc.. may be added to facilitate complexation or to aid in dispersability. The resultant complex is isolated as a dry powder by any process known in the art (co-precipitation and drying, evaporation of the liquid vehicle, spray drying, lyophilization etc..). Particle size may be reduced by any standard technique such as those described previously herein, if desired. The resultant hydrotope complex may be used without further modification or may be compounded into a variety of other formulations or vehicles as required.

Methods of Use

The composition of the present invention, either in oil-based or solvent-derived form, and whether treated to enhance solubility/dispersability or not may be used as an effective agent to lower serum cholesterol in animals, particularly humans. It is to be understood, however, that this composition is equally suited for administration to other animals, for example, in the form of veterinary medicines and animal foods.

1) Pharmaceutical Dosage Forms

It is contemplated within the scope of the present invention that the composition of the present invention may be incorporated into various conventional pharmaceutical preparations and dosage forms such as tablets (plain and coated) for use orally, bucally or lingually, capsules (hard and soft, gelatin, with or without additional coatings) powders, granules (including effervescent granules), pellets, microparticulates, solutions (such as micellar, syrups, elixirs and drops), lozenges, pastilles, ampuls, emulsions, microemulsions, ointments, creams, suppositories, gels, and transdermal patches, modified release dosage forms together with customary excipients and/or diluents and stabilizers.

The composition of tie present invention, adapted into the appropriate dosage form as described above may be administered to animals, including humans, orally, by injection (intra-venously, subcutaneously, intra-peritoneally, intra-dermally or intramuscularly), topically or in other ways. Although the precise mechanism of action is unclear, the composition of the present invention, administered intra-venously, lowers serum cholesterol. It is believed that the phytosterol composition may have, in addition to the role as an inhibitor of cholesterol absorption in the intestine, a systemic effect on cholesterol homeostasis through bile acid synthesis, enterocycte and biliary cholesterol excretion, bile acid excretion and changes in enzyme kinetics and cholesterol transport between various compartments within the body (PCT/CA97/00474 which was published on Jan. 15, 1998). See also paper to Peter Jones (under publication).

2) Foods/Beverages/Nutraceuticals

In another form of the present invention, the composition of the present invention may be incorporated into foods, beverages and nutraceuticals, including, without limitation, the following:

1) Dairy Products—such as cheeses, butter, milk and other dairy beverages, spreads and dairy mixes, ice cream and yoghurt;
2) Fat-Based Products—such as margarines, spreads, mayonnaise, shortenings, cooking and frying oils and dressings;
3) Cereal-Based Products—comprising grains (for example, bread and pastas) whether these goods are cooked, baked or otherwise processed;
4) Confectionaries—such as chocolate, candies, chewing gum, desserts, non-dairy toppings (for example Cool Whip™), sorbets, icings and other fillings;
5) Beverages—whether alcoholic or non-alcoholic and including colas and other soft drinks, juices, dietary supplement and meal replacement drinks such as those sold under the trade-marks Boost™ and Ensure™; and
6) Miscellaneous Products—including eggs, processed foods such as soups, pre-prepared pasta sauces, pre-formed meals and the like.

Either the oil-based or the solvent-derived composition of the present invention may be incorporated directly and without further modification into the food, nutraceutical or beverage by techniques such as mixing, infusion, injection, blending, immersion, spraying and kneading. Alternatively, the composition may be applied directly onto a food or into a beverage by the consumer prior to ingestion. These are simple and economical modes of delivery.

If it is desired to enhance the solubility or dispersability of the composition, whether oil-based or solvent-derived, prior to incorporation into the food, beverage or nutraceutical, this may be achieved by any of the techniques described herein, without limitation.

Without limiting the generality of the foregoing, it is to be understood that depending on the vehicle of delivery, one of the oil-based composition or the solvent-derived composition may be more suitable and efficient for each particular food, pharmaceutical, beverage and nutraceutical use. For example, the solvent-derived composition presents as a solid or semi-solid material which is conveniently suited for use in the pharmaceutical dosage forms described above. Conversely, the liquid oil-based system is conveniently suited for many of the food, beverage and nutraceutical uses described above.

For example, in the formation of emulsions and microemulsions which may readily be incorporated into margarines, butter, spreads, mayonnaise, dressings, yoghurt and the like, the oil-based composition may be more appropriate. Patents covering the preparation of margarines and yellow spreads include: U.S. Pat. Nos.: 5,118,522; 5,536,523; 5,409,727; 5,346,716; 5,472,728; and 5,532,020, all of which are incorporated herein by reference.

Conversely, lower fat content may be achieved in many foods by the incorporation of the solvent-derived composition. This may be particularly important for foods that already have a high fat content.

EXAMPLES

Example 1

Esterification of Phytosterols

A phytosterol mixture (0.60 grams) derived form a vegetable oil was placed in a 25 ml one neck round bottom flask, equipped with a magnetic stirring bar, reflux condenser and a heating bath. Acetic anhydride (10 ml) was added and the reaction mixture was refluxed for 3.5 hours. The mixture was cooled down to room temperature and was stirred at this temperature for 24 hours. The resulting white cake-like material was filtered out, washed with ethyl acetate (2 ml) and dried under vacuo for 24 hours to yield 0.66 g crude mixture.

Example 2

Hydrogenation of Esterified Phytosterols

An esterified vegetable phytosterol crude mixture (0.66 g) was placed in a 100 ml one neck dry round bottom flask with a magnetic stirring bar. Ethyl acetate (30 ml), acetic acid (6.0 ml) and Adam's catalyst (PtO2) were then added. The air atmosphere was replaced with hydrogen atmosphere and the reaction mixture was stirred under hydrogen (atmospheric pressure) and room temperature for 6 hours. The reaction mixture was then filtered to remove the catalyst (quantitatively) and washed with ethyl acetate (2 ml). The resulting solution was evaporated under reduced pressure and dried under vacuo for 24 hours to yield 0.51 g of hydrogenated mixture (77% crude yield).

REFERENCES

1. Law M. R., Wald N. J., Wu., Hacksaw Z A., Bailey A.; Systemic underestimation of association between serum cholesterol concentration and ischemic heart disease in observational studies: Data from BUPA Study; Br. Med. J. 1994; 308:363–366
2. Law M. R., Wald N. J., Thompson S. G.; By how much and how quickly does reduction in serum cholesterol concentration lower risk of ischemic heart disease? Br. Med. J. 1994; 308:367–373
3. La Rosa J. C., Hunninghake D.. Bush D. et al.; The cholesterol facts: A summary of the evidence relating to dietary fats, serum cholesterol and coronary heart disease: A joint statement by the American Heart Association and the National Heart, Lung and Blood Institute. Circulation 1990; 81:1721–1733
4. Havel R. J., Rapaport E.; Drug Therapy: Management of Primary Hyperlipidemia. New England Journal of Medicine, 1995; 332:1491–1498
5. Kuccodkar et al.; Effects of plant sterols on cholesterol metabolism. Atherosclerosis, 1976; 23:239–248
6. Lees R. S., Lees A. M. Effects of sitosterol therapy on plasma lipid and lipoprotein concentrations. In: Greten H (Ed) Lipoprotein Metabolism. Springer-Verlag, Berlin, Heidelberg, New York, 1976:119–124
7. Lees A. M., Mok H. Y. I., Lees R. S., McCluskey M. A., Grundy S. M. Plant sterols as cholesterol-lowering agents: clinical trials in patients with hypercholesterolemia and studies of sterol balance. Atherosclerosis 1977; 28: 325–338
8. Heinemann et al. Effect of low dose sitostanol on serum cholesterol patients with hypercholesterolemia. Atherosclerosis 1986; 61: 219–223
9. Heinemann et al. Comparison of sitosterol and sitostanol on inhibition of intestinal cholesterol absorption. Fourth Cologne Atherosclerosis Conference 1988 Birkhauser Verlag. Basel: 117
10. Augustine R. L. and Reardon Jr. E. J. The palladium catalyzed hydrogenation of cholesterol. Org. Prep and Proced. 1969; 1: 107–109
11. Sreenivasan B. Interesterification of fats. J. Amer. Oil Chemists' Soc. 1978; 55: 796–805

12. Lo. Y. C. and Handel A. P. Physical and chemical properties of randomly interesterified blends of soybean oil and tallow for use as margarine oils. J. Amer. Oil Chemists' Soc. 1983; 60: 815–818
13. Chobanov D. and Chobanova R. Alterations in glyceride composition during interesterification of mixtures of sunflower oil with lard and tallow. J. Amer. Oil Chemists' Soc. 1977; 54: 47–50
14. Attwood D. Microemulsions. In: Colloidal Drug Delivery Systems (J. Kreuter, ed.) Marcel Dekker, New York, 1994:32
15. Eugster C. Rivara G., Forni G. and Vai S. Marigenol-Concentrates comprising Taxol and/or Taxan esters as active substances. Panminerva Med. 1996; 38: 234–242
16. Goldberg A. H. and Higuchi J. J. Pharm Sci. 1968; 57:1583
17. Pharmaceutical Technology: Controlled Drug Release Vol. 1 (M. H. Rubinstein, ed) John Wiley & Sons, New York, 1987, Chapter 10
18. Liposome Drug Delivery Systems, Technomic Publishing Co. Inc., Lancaster, Pa. 1993
19. Pharmaceutical Technology: Liposomes as Drug Delivery Systems Parts I, II, and III, October 1992
20. Wendel S. and Celik M. An overview of spray drying applications. Pharmaceutical Technology; October 1997:124–156
21. Pharmaceutical Dosage Forms: Disperse Systems (Lieberman, Reiger and Banker eds), Marcel Dekker Inc., New York, Basel, Hong Kong. Volume 2
22. Rajewski R. A. and Valentino J. S. Pharmaceutical Applications of Cyclodextrins/In vivo Drug Delivery System. J. Phar. Sci. 1996; 85: 1142–1169

We claim:

1. A composition suitable for incorporation into foods, beverages, pharmaceuticals, and nutraceuticals which comprises one or more esterified and subsequently hydrogenated phytosterols.

2. The composition of claim 1 wherein the phytosterols are selected from the group consisting of sitosterol, campesterol, stigmasterol, brassicasterol, desmosterol, chalinosterol, poriferasterol, clionasterol and all natural or synthesized, isomeric forms and derivatives thereof.

3. The composition of claim 1 additionally comprising a pharmaceutically acceptable carrier material.

4. The composition of claim 1 formed into one of an emulsion or microemulsion.

5. The composition of claim 1 dissolved into an appropriate oil solution.

6. The composition of claim 1 modified to form a delivery vehicle selected from the group consisting of solid dispersions, suspensions, hydrated lipid systems, and inclusion complexations with cyclodextrins, hydrotopes and bile salts.

7. A pharmaceutical formulation for lowering serum cholesterol in animals comprising one or more esterified and subsequently hydrogenated phytosterols.

8. A food comprising one or more esterified and subsequently hydrogenated phytosterols.

9. A beverage comprising one or more esterified and subsequently hydrogenated phytosterols.

10. A method of lowering serum cholesterol in animals which comprises administering to the animal a composition comprising one or more esterified and subsequently hydrogenated phytosterols.

11. A process of making a composition suitable for incorporation into foods, beverages, pharmaceuticals, nutraceuticals which comprises:

condensing an aliphatic acid with one or more phytosterols to form a phytosterol ester; and hydrogenating the phytosterol ester to form a hydrogenated phytosterol ester.

12. The method of claim 11 wherein both steps a) and b) occur in oil.

13. The method of claim 11 wherein both steps a) and b) occur in a solvent selected from an aqueous solvent, organic solvent or a combination of both.

* * * * *